Figure 1:
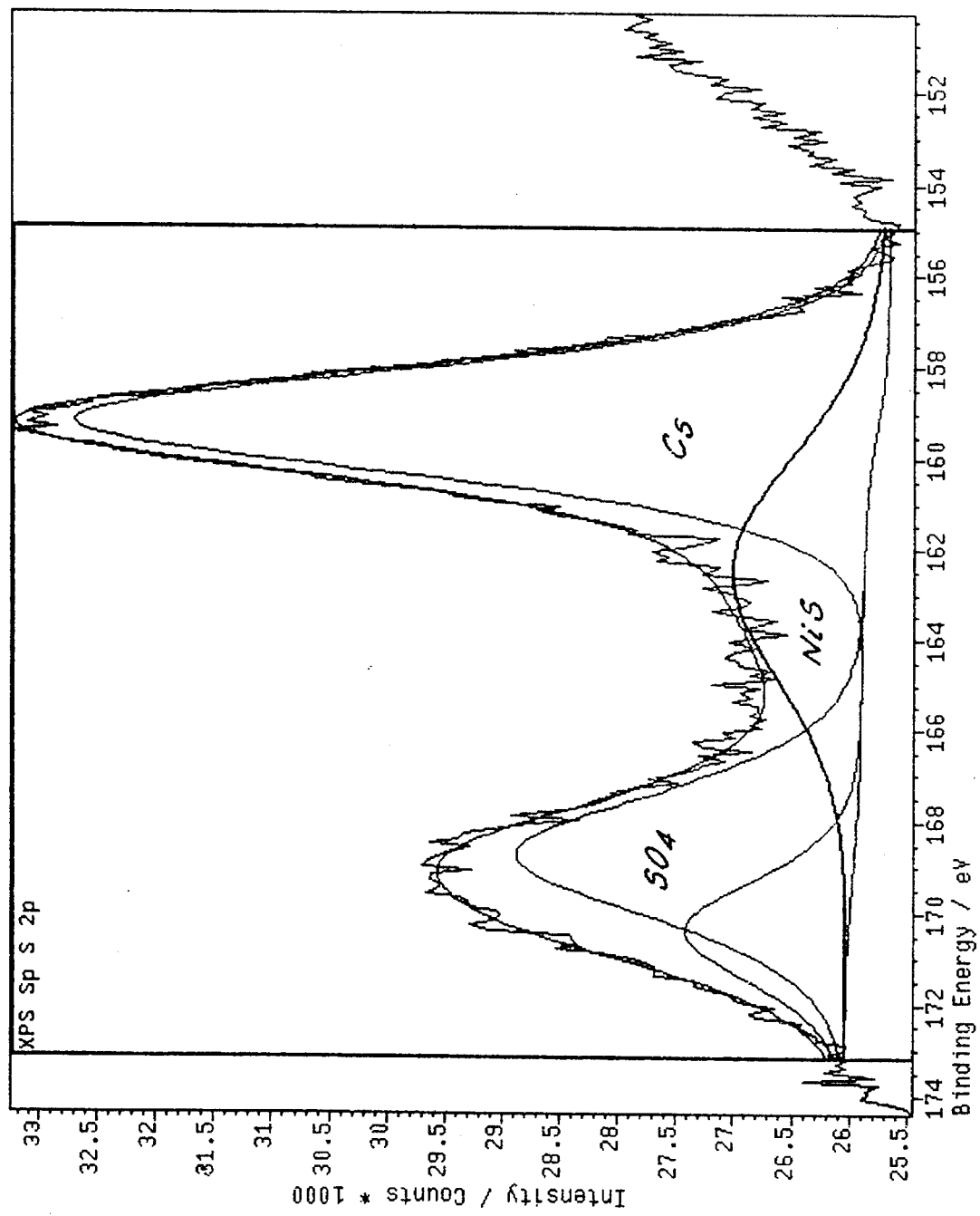

United States Patent [19]

Resasco et al.

[11] Patent Number: 5,489,722
[45] Date of Patent: Feb. 6, 1996

[54] DEHYDROGENATION PROCESSES USING CATALYSTS COMPRISING CATALYTIC METAL ON A NONACIDIC SUPPORT

[75] Inventors: Daniel E. Resasco, Norman, Okla.; Bonita K. Marcus, Radnor, Pa.; Chen-Shi Huang, Claymont, Del.; Vincent A. Durante, West Chester, Pa.

[73] Assignee: Sun Company, Inc. (R&M), Philadelphia, Pa.

[21] Appl. No.: 316,656

[22] Filed: Sep. 30, 1994

Related U.S. Application Data

[63] Continuation-in-part of Ser. No. 874,499, Apr. 27, 1992.

[30] Foreign Application Priority Data

Apr. 20, 1993 [CA] Canada ................................... 2094766
Apr. 27, 1993 [EP] European Pat. Off. ............... 93303257
Apr. 27, 1993 [JP] Japan ..................................... 5-122069

[51] Int. Cl.$^6$ .......................... C07C 5/333; B01J 27/043
[52] U.S. Cl. ........................ 585/661; 585/444; 502/222; 502/66; 502/74; 502/221; 502/259; 502/216
[58] Field of Search ................................... 502/222, 223, 502/66, 74, 221, 259, 216; 585/661, 444

[56] References Cited

U.S. PATENT DOCUMENTS

4,517,306 5/1985 Buss ........................................... 502/74
4,727,216 2/1988 Miller ..................................... 585/661

OTHER PUBLICATIONS

Rennard et al, J. Catalysis, *The Role of Sulfur in Deactivation of Pt/MgAl$_2$O$_4$ for Propane Dehydrogenation*, 96, 235–244 (1986).
Rostrup–Nielsen et al, Catalysis 1987, *Ensemble Control By Sulfur Poisoning of Nickel Catalysts For Steam Reforming*, 725–732, Elsevier Science Publishers B.V., Amsterdam (1988).
Rostrup–Nielsen, J. Catalysis, *Sulfur–Passivated Nickel Catalysts for Carbon–Free Steam Reforming of Methane*, 85, 31–43, (1984).
Rostrup–Nielsen et al., Applied Catalysis 1, *High Temperature Hydrogen Sulfide Chemisorption On Nickel Catalysts*, 303–314, Elsevier Scientific Publishing Company, Amsterdam (1981).
Rostrup–Nielsen et al., J. Catalysis, *Sulfur Poisoning of Boudouard and Methanation Reactions on Nickel Catalysts*, 39, 395–404, (1979).
Rostrup–Nielsen, J. Catalysis, *Equilibria of Decomposition Reactions of Carbon Monoxide and Methane over Nickel Catalysts*, 27, 343–356, (1972).
Bartholomew et al., J. Catalysis, *Chemistry of Nickel–Alumina Catalysts*, 45, 41–53, (1976).
LePage et al., Applied Heterogeneous Catalysis, 5, 110, Gulf Publishing Company (1987).
Mangnus et al., J. Catalysis, *Companion of the Sulfiding Rate and Mechanism of Supported NiO and Ni$^o$ Particles*, 137, 92–101, (1992).
Scheffer et al., J. Catalysis, *A Temperature–Programmed Sulfiding Study of NiO–WO$_3$/Al$_2$O$_3$ Catalysts*, 121, 18–30 (1990).
Swift et al., Ind. Eng. Chem., Prod. Res. Dev., *Elimination of Excessive Carbon Formation during Catalytic Butene Dehydrogenation*, 15, 131–136, (1976).
Stytsenko et al., Kinetics and Catalysis, *Production of Active Surface of a Nickel–Tin Catalyst for Dehydrogenation of Hydrocarbons*, Plenum Publishing Corporation, 802–807 (1988).
Agnelli et al., Catalysis Today, *Surface Organometallic Chemistry on Metals Preparation of New Selective Bimetallic Catalysts by Reaction of Tetra–n–Butyl Tin with Silica Supported Rh, Ru and Ni*, 6, 63–72, (1989).

*Primary Examiner*—Asok Pal
*Attorney, Agent, or Firm*—Q. Todd Dickinson; Stephen T. Falk

[57] ABSTRACT

Organic compounds are dehydrogenated by contact with a catalyst prepared by oxidizing and then sulfiding a composition comprising Group VIIIA (first or second row) catalytic metal on a nonacidic porous support, for example alumina, to produce compositions which have good dispersion of a catalytically active metal component and of sulfide species over the surface of the compositions and high activity as catalysts for the dehydrogenation of organic compounds. In one embodiment of the invention the catalyst used in the process of the invention has ratios of nickel, and/or sulfide species to peak areas of aluminum in the support, as determined by X-ray photoelectron spectroscopy (XPS), which improve their activity and stability for use as dehydrogenation catalysts. The catalyst may also have ratios of cesium, added to reduce acidity, to aluminum peak areas, as determined by XPS, which have advantages for use as dehydrogenation catalysts in respect of activity, resistance to deactivation and avoidance of side reactions.

25 Claims, 5 Drawing Sheets

DEHYDROGENATION PROCESSES USING CATALYSTS COMPRISING CATALYTIC METAL ON A NONACIDIC SUPPORT

This application is a continuation-in-part of application Ser. No. 07/874,499, filed Apr. 27, 1992, now allowed which discloses and claims inter alia the dehydrogenation of alkanes, for example isobutane, using as catalyst sulfided nickel supported on nonacidic supports.

BACKGROUND AND PRIOR ART

The increasing demand for certain olefins as chemical intermediates for the production of oxygenates and alkylates for motor fuels, coupled with the plentiful supply of lower alkanes, provides incentive for the use of catalytic dehydrogenation on an industrial scale: E. Chang, in "Alkane Dehydrogenation and Aromatization", Report No. 203, SRI International, Calif., Menlo Park, 1992.

Driven largely by the rapid growth in demand for tertiary alkyl ethers, the dehydrogenation of isobutane or isopentane to isobutylene or isoamylene respectively is receiving renewed attention since branched ethers are prepared by etherification of branched olefins with methanol or ethanol.

The dehydrogenation reaction is currently carried out in commercial processes in the vapor phase over chromia-alumina or noble-metal catalysts. Due to the endothermic nature of this reaction and the normally unfavorable equilibrium, elevated process temperatures are necessary to reach economically acceptable levels of conversion. These severe operating conditions favor coke formation and catalyst deactivation. As a consequence, most of the commercial processes for dehydrogenation of lower alkanes require feeds diluted with hydrogen or steam and short reaction cycles with frequent regenerations: Chang, supra; A. J Horsley,in "Catalytic Dehydrogenation and Oxidative Dehydrogenation", Catalytica Study No. 4190 DH. Catalytica, Calif., Mountain View 1991. Improved process economics could result from the development of catalysts that perform well under severe conditions for conditions.

Previous workers have shown that the addition of small amounts of sulfur to certain metallic catalysts has beneficial effects on selectivity and coke formation. For example, R. J. Rennard, and Freel, J. Catal., 98, 235 (1986) have shown that sulfur causes an increase in propylene yield over Pt-Re catalysts upon sulfiding. The effect of sulfur in reducing the rate of coke formation has been reported by Rostrup-Nielsen and co-workers: J. R. Rostrup-Nielsen, and I. Alstrup, in "Catalysis 1987" (J. W. Ward, Ed.) p. 725, Elsevier, Amsterdam, 1988; Rostrup-Nielsen, J. Catal., 85, 31 (1984); Alstrup, Rostrup-Nielsen, and S. Roen, S. Appl. Catal., 1, 303 (1981); Rostrup-Nielsen, and K. Pedersen, J. Catal., 59, 395 (1979); and Rostrup-Nielsen, J. Catal., 27, 343 (1972), for Pt-Re catalysts and for the case of steam reforming. The presence of half a monolayer of sulfur on the Ni surface strongly inhibited the rate of carbon deposition, while it did not inhibit the rate of steam reforming to the same extent. This effect has been explained in terms of the ensemble of atoms required to constitute the active site for each reaction. The ensemble for the steam reforming reaction is smaller than that required for coke formation. Consequently, although both rates decreased when sulfur was added, the coking rate did so almost 10 times faster than the reforming rate.

Reducing nickel-impregnated alumina in hydrogen without prior calcination in air resulted in greater nickel surface area and dispersion than found in those catalysts obtained by reduction with prior calcination in air; C. H. Bartholomew and R. J. Farrauto, "Chemistry of Nickel-Alumina Catalysts", Journal of Catalysis, 45, 41 (1976).

Calcining nickel-impregnated catalyst prior to reduction in hydrogen is disclosed in J. F. LePage et al, "Applied Heterogeneous Catalysis", page 110, Gulf Publishing Company, Houston (1987).

The mechanisms of sulfiding pre-reduced and pre-oxidized nickel particles have been studied by P. J. Mangnus, E. K. Poels, A. D. Langeveld and J. A. Moulijn, "Comparison of the Sulfiding Rate and Mechanism of NiO and $Ni^0$ Particles", Journal of Catalysis, 137, 92 (1992). Commercial theta-alumina-supported nickel catalysts were reduced to Ni and sulfided. A green NiO catalyst based on alpha-alumina was calcined and then sulfided.

NiO "well dispersed" and relatively strongly bound on a gamma-alumina support is disclosed in B. Scheffer, P. J. Mangnus and J. A. Moulijn, in Journal of Catalysis, 12, 18 (1990).

Sulfiding catalytic nickel in situ as formed in the dehydrogenation of butene with a nickel-phosphate containing catalyst is disclosed in H. E. Swift, H. Beuther and R. J. Rennard, "Elimination of Excessive Carbon Formation During Catalytic Butene Dehydrogenation", Ind. Eng. Chem., Prod. Res. Dev., 15, No. 2, pages 131–135 ((1976).

A compound containing reduced or oxidized nickel on kieselguhr used in catalysis of dehydrogenation and hydrogenolysis of cyclohexane is disclosed in V. D. Stytsenko et al, "Production of Active Surface of a Nickel-Tin Catalyst for Dehydrogenation of Hydrocarbons", in "Kinetics and Catalysis", Consultants Bureau, New York, Plenum Publishing Corporation, pages 802–807 (1988).

Catalysts containing nickel in an oxidized or reduced state are disclosed in M. Agnelli et al, "Surface Organo-metallic Chemistry on Metals. Preparation of New Selective Bimetallic Catalysts by Reaction of Tetra-n-butyl Tin With Silica Supported Rh, Ru and Ni", in Catalysis Today, 9 (1989) 63–72.

DESCRIPTION OF THE INVENTION

It has been found that dehydrogenation processes using certain catalysts as described below are capable of superior performance to prior art dehydrogenation processes. In the process of the invention, dehydrogenatable organic compounds are dehydrogenated by contact with such catalysts under dehydrogenation conditions. Suitable materials for dehydrogenation using the process of the invention include the dehydrogenatable alkanes such as ethane, propane, butanes, hexanes and the like, dehydrogenatable cycloalkanes such as cyclohexane and the like, alkyl-substituted ring compounds such as alkylcyclohexanes, alkylbenzenes, alkylnaphthalenes and the like, and other dehydrogenatable compounds as known in the art. Typical reaction temperatures in the dehydrogenation processes of the invention are in the range from about 500° to about 750° C. The dehydrogenation may be conducted at atmospheric or elevated pressure. The hydrocarbon/hydrogen volume ratio is preferably in the range from 0.1 to 1.5 in order to optimize the rate of dehydrogenation relative to the rate of deactivation, see FIG. 7 of the drawings, but other volume ratios may be used.

In one embodiment of the dehydrogenation process of the invention, the catalyst used in the process is prepared in the following manner: a composition comprising a catalytic metal selected from the group consisting of Group VIA, Group VIIIA first row and Group VIIIA second row metals, and a nonacidic microporous support, is oxidized to obtain an oxidized composition, which is then sulfided to obtain the catalyst used in the process of the invention.

In another embodiment of the process according to the invention, the catalyst used in the process is a novel composition of matter which comprises sulfided nickel and nonacidic alumina and which has:

(1) a ratio of the nickel $2P_{3/2}$ peak area to the Al(2s) peak area, as determined by X-ray photoelectron spectroscopy (XPS) (hereinafter "Ni/Al XPS ratio"), of at least about 0.7, preferably at least about 0.8, and/or (2) a ratio of the sulfide $S^{2-}$(2p)/Alpeak area to the Al(2s) peak area, as determined by XPS (hereinafter "S/Al XPS ratio" or "$S^{2-}$/Al ratio"), of at least about 0.05, preferably at least about 0.06, more preferably at least about 0.07.

In one embodiment the composition comprises also a base, and when the base is a cesium compound, the composition has a ratio of the cesium $4P_{3/2}$ peak area to the Al(2s) peak area, as determined by XPS (hereinafter "Cs/Al XPS ratio"), of at least about 0.07, preferably at least about 0.08, more preferably at least about 0.1.

These novel compositions of matter are disclosed and claimed in copending application Ser. No. 08/316,659 filed Sep. 30, 1994.

X-RAY PHOTOELECTRON SPECTROSCOPY

XPS is a surface-sensitive technique by which a material is analyzed to determine peak areas at binding energy electron-volt (eV) levels which are characteristic of the individual atomic constituents of the material. To make such determinations, for the purposes of the present invention, an instrument having an instrument transmission function inversely proportional to the kinetic energy of photoelectrons, is used. Such an instrument is a Kratos "Xsami" instrument equipped with a dual-anode X-ray source and a reactor for in situ treatments, for example. Binding energy measurements are referenced to Al(2s)=119.2 eV. Data reduction may be carried out using "Vision" software provided by Kratos. Where XPS ratios are referred to herein, it is understood that such ratios are expressed in terms characteristic of instruments having instrument transmission function as referred to above. The use of XPS in characterizing compositions according to the invention is disclosed in D. E. Resasco, B. K. Marcus, C. S. Huang and V. A. Durante, "Isobutane Dehydrogenation over Sulfided Nickel Catalysts", Journal of Catalysis 146, 40–55 (1994).

PREPARATION OF DEHYDROGENATION CATALYSTS

The process of the invention uses in one embodiment a catalyst obtained by oxidizing a composition comprising a catalytic metal selected from the group consisting of Group VIA, Group VIIIA first row and Group VIIIA second row metals and a nonacidic microporous support, to obtain an oxidized composition, and sulfiding the oxidized composition.

It has been found that dehydrogenation processes using as catalysts the compositions thus prepared are capable of superior performance to dehydrogenation processes using as catalysts compositions which have been similarly prepared except that they have been reduced and sulfided, rather than oxidized and sulfided, and of greatly superior performance to dehydrogenation processes using as catalysts nonsulfided compositions, i.e., compositions which have been similarly prepared except that they have not been sulfided.

The starting material for preparing a catalyst for use in the process of the invention is a microporous support, for example alumina, on which a catalytic metal, for example nickel, has been deposited, and which is initially nonacid, or which has been treated with a base, to reduce the acidity thereof.

SUPPORT

The support used in preparing a catalyst for use in the process of the invention may be any nonacidic support, or may be a support which has been treated to reduce acidity either before, during or after incorporation of catalytic metal into the catalyst. Useful supports include leached aluminas of reduced acidity, silicas, zirconias, titanias, magnesias, chromium-treated silicas or silica-titanias, tantalum-doped zirconias, non-acidic forms of zeolites, such as base treated mordenites or barium-exhanged zeolites, microporous aluminum phosphates, nonacidic forms of SAPO's (silicoaluminum phosphates), silicoferrates, silicoborates, silicotitanates, other nonacidic molecular sieves, basic clays, magnesium-aluminate spinels, zinc aluminates, carbon-coated supports, ceramics, and other supports known in the art.

In preparing zeolite supports, ion exchange or impregnation methods to remove or reduce protonic acidity are effective. Base treated mordenite or barium exchanged zeolite L are useful supports for example. In the case of barium exchanged L zeolite, for example, repetitive ion exchange and calcination steps are required to reduce acidity substantially. After incorporation of catalytic metal, sulfiding, and activation, sufficiently basic and/or nonacidic supports result in virtually no isomerization and little hydrogenolysis of isobutane under laboratory test reaction conditions in which two moles of hydrogen are cofed per mole of isobutane at 600° C. over a 10 ml bed of catalyst held isothermally.

NONACIDIC SUPPORT

The support used in the process of the invention is nonacidic, which may include a slight acidity, substantially reduced from the acidity of alumina for example. Preferably, the support has no acidity as measured by temperature programmed desorption (TDP) of preadsorbed pyridine, since any degree of acidity may substantially affect the life of the catalyst in use in dehydrogenation processes.

CATALYTIC METAL

The catalyst used in the process of the invention may contain any metal having catalytic activity for dehydrogenation processes. Preferably, the metal is a Group VIIIA first-row or second-row metal, more preferably nickel, palladium and rhodium, or mixtures of such metals with each other and/or with other metals.

TREATMENT WITH A BASE

Preferably, the support used in the catalyst for use in the process of the invention is an alumina which has been treated with a base, to reduce its acidity. Any suitable base may be used in this embodiment of the invention, for example alkali metal, alkaline earth metal hydroxides or carbonates or the like. Preferably, the base is non-volatile. Alkali metal compounds are preferred bases for use according to the invention. Such compounds may be selected from the group of compounds or allotropes of cesium, rubidium, potassium, sodium, lithium or francium, or mixtures thereof. Potassium, rubidium or cesium, or mixtures thereof are preferred. The basic component reduces surface acidity of the composition and reduces coking and hydrogenolysis and isomerization reactions in the use of the composition as a catalyst in dehydrogenation processes. Preferably the basic component is well dispersed throughout the catalyst.

The addition of the basic component may be accomplished by impregnation before or after the incorporation of the catalytic metal, or in a co-impregnation step. The base may also be incorporated by a co-precipitation method which, at least in the case of alkali metal and alumina, often results in a mixed alumina-alkali structure after calcination. Other methods of incorporating the base are co-gelation and ion exchange. Preferably the base is added separately from the catalytic metal in order to non-homogeneously distribute the metal with regard to pore structure yet uniformly deposit the base on the support surface.

The preferred base loading depends on the method of incorporation and the surface area of the support. When using cesium as the cation, typically useful ranges are 1 to 8 weight percent cesium loading. Preferred cesium loading for a 90 $m^2/g$ support is 5 to 7% by weight.

OXIDATION STEP

The oxidation of a composition comprising catalytic metal and a nonacidic microporous support, in the preparation of a catlayst for use in the process of the invention, is done by contacting the composition with an oxidizing agent under oxidizing conditions. A preferred oxidizing agent is molecular oxygen in a dilute stream, and preferred oxidizing conditions comprise temperatures in the range from about 250° to about 375° C. Other known methods for oxidizing metals, for example, nickel, to metal oxides may be employed.

SULFIDING OF OXIDIZED COMPOSITION

The sulfiding of the oxidized composition obtained as described above is done by contacting the oxidized composition with a sulfur-containing material under sulfiding conditions. Preferably, a sulfur-containing organic compound is used as the sulfiding agent, more preferably dimethylsulfoxide. Hydrogen sulfide, although useful, is less desirable than DMSO as a sulfiding agent to achieve a highly stable catalyst. Typical sulfiding conditions comprise temperatures in the range from about 200° to about 600° C. Preferably, the sulfiding is done in a hydrogen atmosphere, in order to obtain particularly good dehydrogenation activity and/or resistance to deactivation of the catalyst.

CATALYST

Compositions used as catalysts in the process of the invention are active and selective as dehydrogenation catalysts for relatively long reaction times and optionally under low hydrogen/hydrocarbon ratios, important advantages compared to the existing technology. Though the invention is not to be limited by any theory, the sulfided metal component present in these catalysts is viewed as distinct from zero-valent metal per se, and distinct from zero-valent metal modified by the presence of chemisorbed sulfur. The active component of the catalyst according to the invention is believed to be neither zero-valent catalytic metal nor a bulk sulfide of the catalytic metal, but rather a surface sulfide of the catalytic metal.

ADVANTAGES OF PARTICULAR CATALYSTS

It has been found that sulfided nickel and nonacidic alumina compositions having Ni/Al XPS ratio of at least about 0.7 have superior activity as dehydrogenation catalysts to that of such compositions having Ni/Al XPS ratio less than about 0.6. The superior activity may be caused by better dispersion of the active nickel sulfide component on the surface of the composition in the compositions according to the invention, as compared to compositions wherein the Ni/Al XPS ratio is lower.

It has further been found that sulfided nickel nonacidic alumina compositions having S/Al XPS ratio of at least about 0.06 have superior activity as dehydrogenation catalysts to that of such compositions having S/Al XPS ratio less than about 0.05. The superior activity may be caused by better dispersion of the specific sulfide species which is catalytically active on the surface of the compositions according to the invention, as compared to compositions wherein the S/Al XPS ratio is lower or reflective of a less active or inactive sulfide phase.

It has further been found that sulfided nickel cesium alumina compositions having Cs/Al XPS ratio of at least about 0.07 have superior activity as dehydrogenation catalysts to that of such compositions having ratio of the cesium $4P_{3/2}$ peak area to the Al(2s) peak area less than about 0.06. The superior activity of the compositions according to the invention as may result from better dispersion of cesium on the surface of the catalyst, as compared to compositions wherein the Cs/Al XPS ratio is lower.

SEVERELY DEACTIVATING CONDITIONS

The catalysts used in the process of the invention are particularly suitable for use as dehydrogenation catalysts under severely deactivating conditions. Severely deactivating conditions comprise operation at temperatures of greater than about 530° C., at hydrogen/hydrocarbon feed ratios of 2 or less, and/or with more than about 90 hours on stream between regenerations.

In order to adapt the process of preparing such catalysts, which involves oxidizing and sulfiding a composition comprising catalytic metal on a nonacidic porous support, to processes for making a catalyst which is particularly suitable for dehydrogenation of dehydrogenatable compounds under severely deactivating conditions, the following may be done:

(1) Adjust the pore size distribution of the support by leaching and calcining the support phase. Since (a) coke preferentially deposits in pores having radius of 20 to 50 angstroms, and since (b) pores having radius of about 50 to about 200 angstroms contribute significantly to surface area of the catalyst, yet are not as susceptible as the 20 to 50 angstrom pores to blockage by coke, and since (c) pores having radius greater than about 200 angstroms do not significantly enhance performance and may physically weaken the structural integrity of the particles, the support according to this embodiment of the invention preferably has pore volume in the 20 to 50 angstrom range which is less than about 0.1 ml/g, and more preferably less than about 0.05 ml/g, and has pore volume in the 50 to 200 angstrom range from about 0.3 to 1.5 ml/g, more preferably about 0.4 to 0.8 ml/g.

Carboxylic and dicarboxylic acids, for example succinic acid and malonic acid, may be used to selectively dissolve a support such as alumina in the preferred porosity region and produce a support having the preferred porosity characteristics as disclosed above. Oxalic acid may be used but is not preferred. Diacids containing more than 6 carbon atoms are less favorable but may be used with some modification of time, temperature and concentration conditions from those used with the preferred reagents. After leaching, filtering, washing and drying, the catalyst is calcined, for example at about 700° to 1100° C. for a time sufficient to reduce the microporosity of the catalyst below that of the catalyst before the leaching treatment.

The preferred sequence of steps in this embodiment of the invention is selective leaching of support with diacid, impregnation of the support with a basic material if it is not already nonacidic, impregnation with catalytic metal, oxidation, and sulfiding.

(2) Deposition of catalytic metal more in the larger pores of the support than in the smaller pores of the support. This may be done by temporarily filling the smaller pores with an organic liquid which has low solubility in the solution which is to be used to deposit the catalytic metal on the support; then the support is impregnated with the solution, then dried and calcining. Since the organic liquid preferentially fills the smaller pores, the solution of the catalytic metal preferentially impregnates the larger pores of the support. The preferred sequence of steps is: impregnation of support with a basic material if the support is not already nonacidic, filling of smaller pores with organic liquid, impregnation with catalytic metal, oxidation, and sulfiding.

(3) Optional formation of a carbonaceous layer between the support and the catalytic metal. This may be done before depositing catalytic metal on the support. The support is contacted under carbonizing conditions with a carbonizable substance to obtain a support with a carbonaceous layer thereon. Typically, the product of this step comprises about 0.2 to 6, preferably about 0.4 to 4, more preferably 1.5 to 2.5, weight percent carbon. The carbonaceous layer may comprise some hydrogen and oxygen, but the hydrogen to carbon atomic ratio is preferably less than about 0.2, and the oxygen to carbon ratio is preferably about 0.001 to 0.16 atomic ratio.

The carbonaceous layer may, for example, be applied to the support of appropriate pore structure by thermal pyrolysis of a vaporized stream of $C_3$ to $C_5$ alkene such as isobutene at about 700° to 800° C. Additional thermal pyrolysis of the carbonized solid under a flowing nitrogen atmosphere without feeding additional hydrocarbon may be conducted to reduce the hydrogen to carbon ratio to the desired level. The catalytic metal is applied to the carbonized support by impregnation, for example, with a solution, in the case of nickel as the catalytic metal, of nickel nitrate in acetone. After evaporation of acetone, the nickel-containing solid is, for example, pyrolyzed under nitrogen at 500° C. The preferred sequence of steps comprises formation of carbonaceous layer on support, impregnation with catalytic metal, impregnation with alkali metal, oxidation, and sulfiding.

The process of the invention, using catalysts prepared in the above ways, may provide in respect to the catalyst greater activity retention, greater resistance to pore plugging by coking, lowered tendency toward isomerization reactions, and ease of regeneration.

A major advantage of catalysts thus prepared is their ability to actively and highly selectively dehydrogenate alkanes for long times on stream without need for frequent regenerations when used under severely deactivating conditions, which are conditions of high temperature and low hydrogen-to-hydrocarbon feed ratios and/or with use of feeds containing sulfur impurities. To best deal with these conditions, the pore size distribution of the alumina may be adjusted as described above. Such adjustment is required in order to produce the most stable catalysts (coke-tolerant catalysts) useful under severely deactivating conditions.

EXAMPLES OF PREPARATION OF COMPOSITIONS ACCORDING TO THE INVENTION

A supported catalyst was prepared by the following sequences of impregnations and thermal treatments.

Impregnation with cesium: A gamma-alumina support CS-331-4 from United Catalysts was first calcined at 950° C. for 10 hrs. in air. The pore volume of this material as determined by nitrogen adsorption was 0.7 cc/g.

To obtain incipient wetness conditions during impregnation, the ratio between the volume of the impregnating solutions and catalyst weight was kept at 0.7 cc/g. To incorporate 5 wt % cesium, the support was impregnated with an aqueous solution of cesium nitrate. After this impregnation the solid was dried in air at 150° C.

Impregnation with nickel: Subsequently 6 wt % Ni was incorporated by impregnation with a solution of nickel nitrate in acetone. Finally, the catalyst was dried at 150° C. and stored until needed for sulfiding. The catalyst precursor thus prepared is designated here as Catalyst A.

Catalyst A was subjected to three different sulfiding procedures on separate aliquots.

Sulfiding of pre-reduced catalyst in hydrogen (Procedure 1): The catalyst was reduced in hydrogen using a temperature ramp of 3° C./min. up to 600° C. After 2 hrs. at 600° C. (873° K.) the catalyst was sulfided in hydrogen by addition of dimethyl sulfoxide (DMSO) in a S:Ni ratio of 1:1. The product was designated Procedure 1 catalyst.

Sulfiding of pre-oxidized catalyst in nitrogen (Procedure 2): Catalyst A was oxidized under a 1% oxygen in nitrogen stream at 300° C. (573° K.) for 2 hrs. Then it was sulfided in two steps under a nitrogen stream at 200° C. and 400° C. by addition of DMSO in a S:Ni weight ratio of 0.5:1 each time. The product was designated Procedure 2 catalyst.

Sulfiding of pre-oxidized catalyst in hydrogen (Procedure 3): Identical to Procedure 2, except that the addition of DMSO was done under a hydrogen stream. The product was designated Procedure 3 catalyst.

CHARACTERIZATION OF CATALYST

The state of the catalysts after the different sulfiding procedures was analyzed by XPS. A comparison of the ratio between the Ni and Al signals on the three different samples is made in Table 1.

TABLE 1

| Nickel, sulfide and cesium distribution over the support surface as determined by XPS | | | |
|---|---|---|---|
| Procedure | Ni/Al Ratio | $S^{2-}$/Al Ratio | Cs/Al Ratio |
| 1 | 0.60 | 0.03–4 | 0.11 |
| 2 | 1.25 | 0.08 | 0.06 |
| 3 | 0.86 | 0.08 | 0.10 |

The data in Table 1 show that the catalysts that had been pre-oxidized before sulfiding (Procedures 2 and 3) exhibited higher Ni/Al ratios than the pre-reduced catalyst (Procedure 1). Since the amount of Ni on the three samples was the same, a higher Ni/Al ratio indicates a better dispersion of a sulfided nickel phase over the surface.

DRAWINGS

Figure 2:
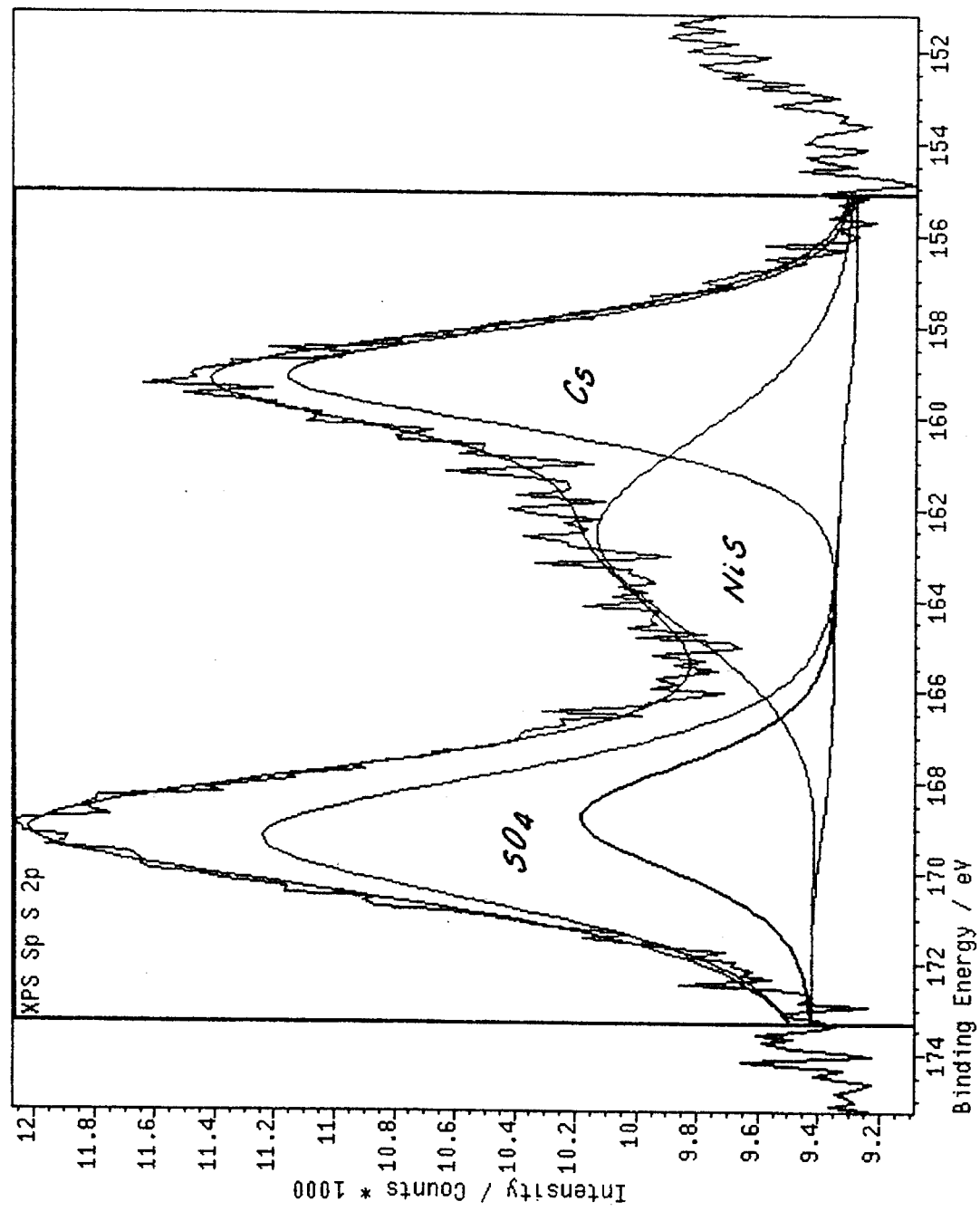
Figure 3:
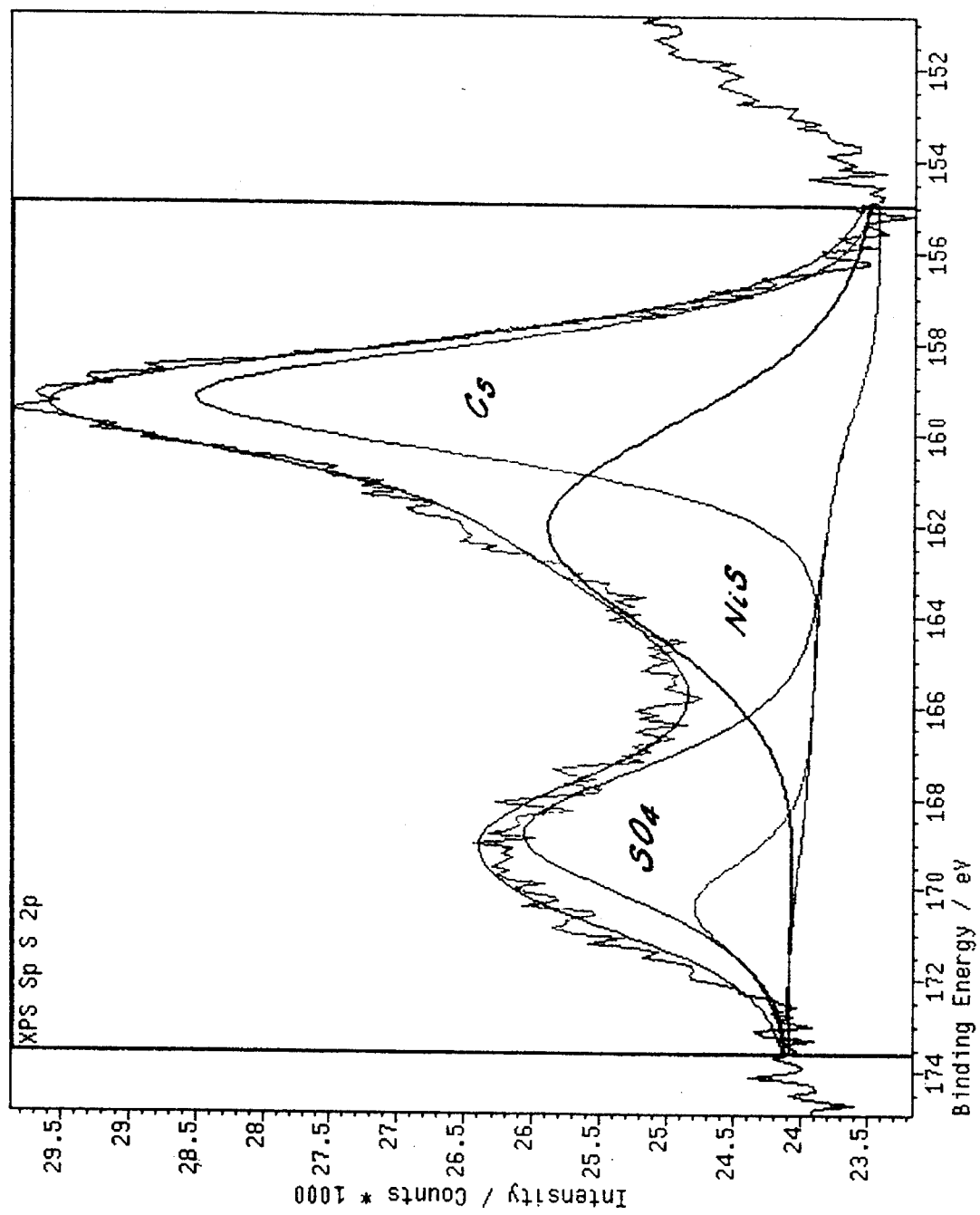

FIGS. 1, 2 and 3 of the drawings show the XPS spectra of sulfur species for Ni-Cs alumina catalysts prepared by the procedures above, 1, 2 and 3. In FIG. 1, the preparation involved reduction in hydrogen at 600° C. and sulfiding with dimethyl sulfoxide (DMSO) in hydrogen at 600° C. In FIG. 2, the preparation involved oxidation at 300° C. and sulfiding with DMSO in nitrogen at 200° C. and 400° C. In FIG. 3, the preparation involved oxidation at 300° C. and sulfiding with DMSO in hydrogen at 200° C. and 400° C.

Figure 4:
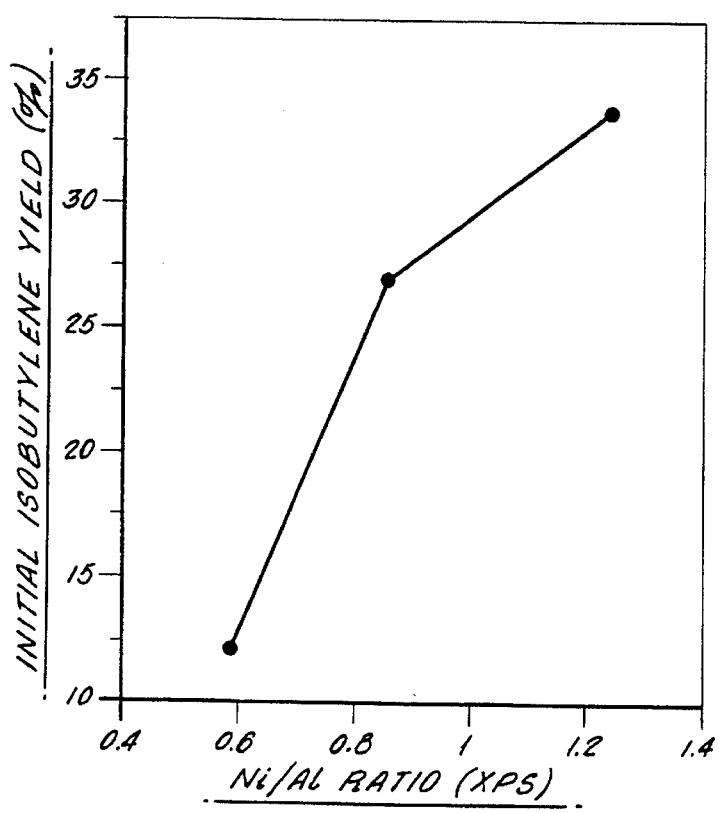
Figure 5:
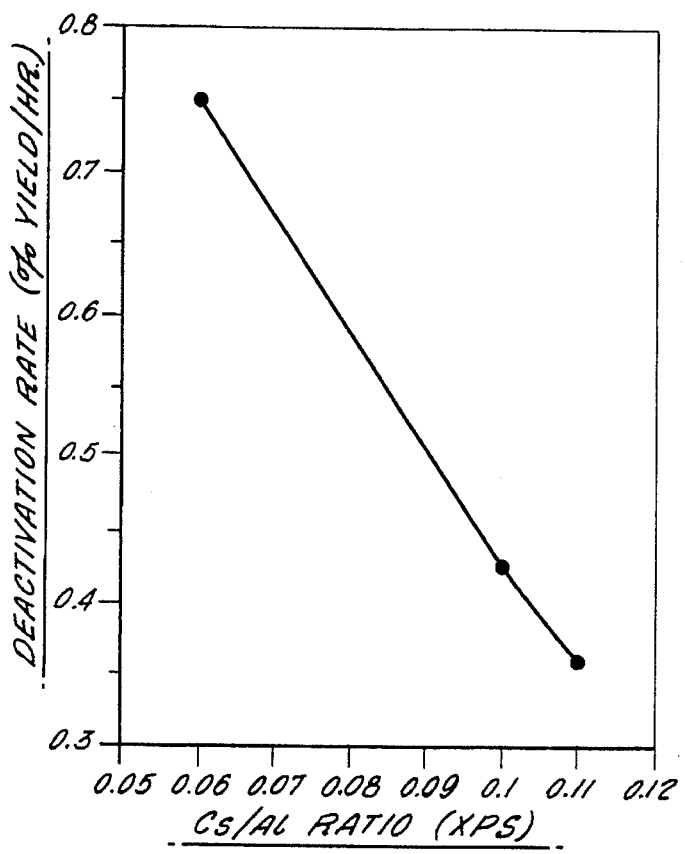

FIG. 4 of the drawings shows graphically the correlation between nickel dispersion and dehydrogenation activity for the catalysts prepared by the procedures above, and FIG. 5 shows the correlation between Cs dispersion and deactivation for those catalysts under isobutane dehydrogenation conditions.

Figure 6:
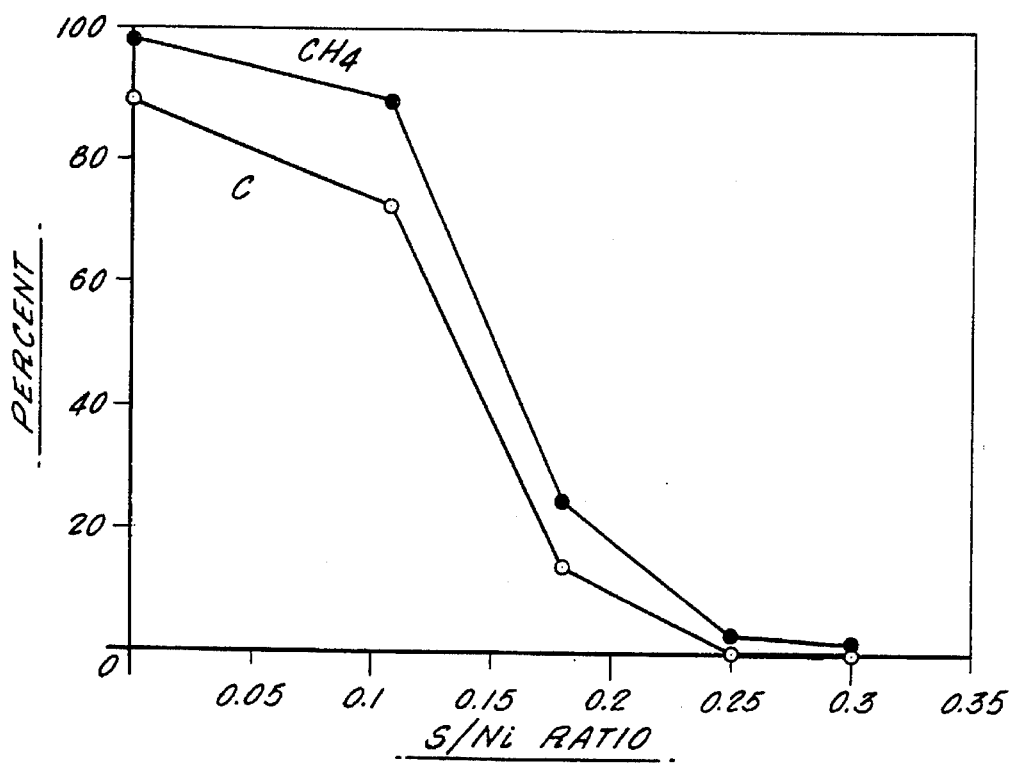

FIG. 6 of the drawings shows the effect of the ratio of sulfur to nickel on the catalyst on the percent carbon and percent $CH_4$ produced in dehydrogenation of isobutane over Ni/Cs-$Al_2O_3$ catalyst at 600° C. and $H_2$/isobutane molar ratio of 1/2.

Figure 7:
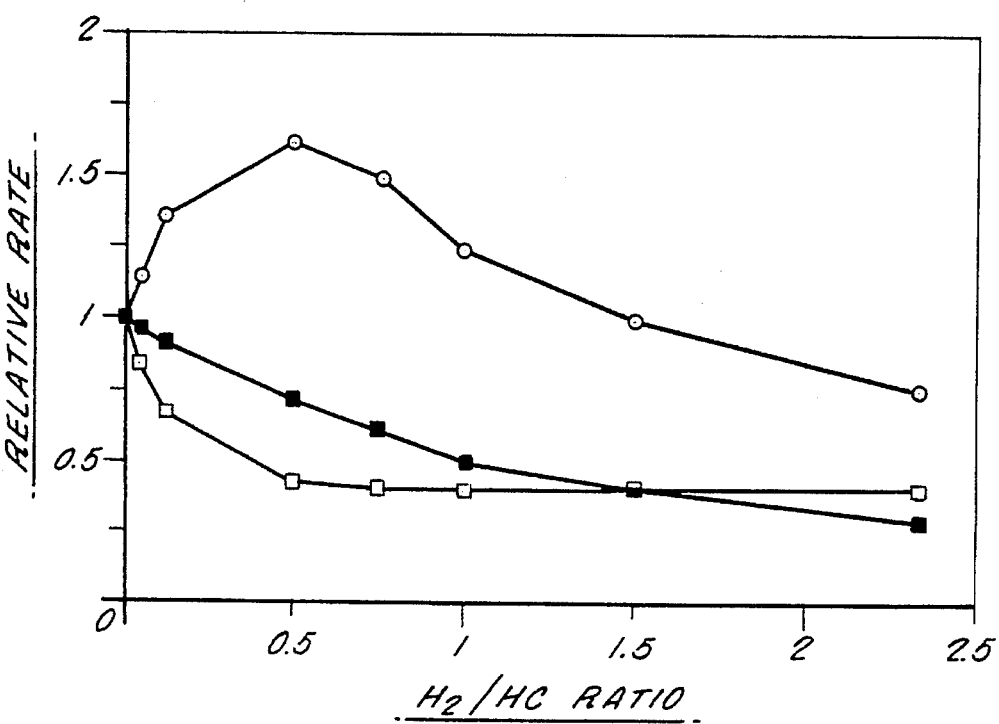

FIG. 7 of the drawings shows the effect of the hydrogen/isobutane ratio on the relative rates of dehydrogenation of isobutane and of deactivation of a 3% nickel 5% cesium on alumina dehydrogenation catalyst.

FIGS. 1, 2 and 3 show that the relative heights of the alkali metal peak, the $SO_4$ peak and the NiS peak in XPS are affected by the catalyst preparation method, in particular by whether the catalyst is sulfided in hydrogen.

A further conclusion can be inferred from the analysis of the sulfur species. Comparing the XPS spectra of the S peaks of the three samples in FIGS. 1, 2 and 3, two sulfur species are clearly observed next to the Cs signal. The peak at a binding energy of about 162.3 eV is attributed to sulfide, $S^{2-}$, while the peak at 170.5 is attributed to sulfate, $(SO_4)^{2-}$. Comparison of the relative magnitude of these peaks indicates that the pre-oxized catalyst sulfided in a hydrogen atmosphere (FIG. 3) achieved a higher concentration of nickel sulfide species on the surface than the catalyst which was not pre-oxidized (FIG. 1) and the catalyst which was pre-oxidized and sulfided in nitrogen (FIG. 2). Thus, pre-oxidation and sulfiding in hydrogen not only result in better dispersion of nickel, but in a greater concentration of the presumed active species.

CATALYST ACTIVITY MEASUREMENTS

The catalytic properties of the three samples prepared by the different sulfiding procedures were investigated in a fixed bed flow reactor. The dehydrogenation of isobutane to isobutylene was used as a test reaction. The tubular reactor had passivated stainless steel walls with an internal diameter of ½ inch. Passivation was accomplished by repeated exposure of the empty reactor to $H_2S$, DMSO, and $H_2$ mixtures at 873° K. prior to activity measurements. The catalyst bed volume was constant for all the runs at 17 $cm^3$. For runs used to study nonsulfided catalysts, nonpassivated reactors constructed of 316 stainless steel were used. This reactor was operated isothermally at 873° K. and controlled within 1° K. by a temperature controller through a PID loop. Isobutane was fed through a liquid metering pump into a thermostated packed preheating chamber. The isobutane gas flow was kept constant at 280 ml/min NTP. Hydrogen flow was controlled by a mass flow controller and varied from 0 to 560 ml/min NTP. Before each run the catalysts were reduced and sulfided with DMSO. After sulfiding, the catalyst was left under hydrogen at 873° K. for an additional 1 hr. before the introduction of the hydrocarbon feed. The hydrogen to hydrocarbon ratio was varied between 0 and 6. After each reaction run in the flow reactor, the total amount of carbon deposited on the catalyst was determined using a LECO carbon analyzer. Reaction products were analyzed off line in a gas chromatograph. Selected gas samples were analyzed by GC-MS. The data from both analytical methods were in excellent agreement, and the reproducibility of the data obtained from the different runs on the same sample was within 10%. The steady state conditions of the feed were reached in less than 15 min., but the catalysts exhibited activation periods of several hours before achieving their maximum activity.

TABLE 2

Isobutane dehydrogenated over sulfided Ni/Cs-alumina. Catalytic activity data in a flow reactor at 600° C.

| Procedure | Initial Conversion C molar % | Selectivity | | |
|---|---|---|---|---|
| | | D | H C mol % | I |
| 1 | 13.0 | 96 | 4 | 0 |
| 2 | 35.9 | 93.5 | 5.3 | 1.2 |
| 3 | 23.1 | 96.2 | 3.8 | 0 |

D = dehydrogenation
H = hydrogenolysis and cracking
I = isomerization

Table 2 shows the results of dehydrogenation at atmospheric pressure and 600° C. The total flow rate was 250 cc/min. and the gas hourly space velocity was 885 $hr^{-1}$ for the three samples investigated. No significant difference in selectivity for dehydrogenation was observed in the three samples. On the other hand, there were significant differences in overall conversion. The samples that had been pre-oxidized before the sulfiding (Procedures 2 and 3) exhibited a much higher initial activity than the one pre-reduced sample. The observed trend in catalytic activity can be explained in terms of concentration of surface species.

As illustrated in FIG. 4, the initial activity correlates well with the dispersion of an active phase of Ni. Table 3 presents the data of FIG. 4 in tabular form.

TABLE 3

| Procedure | Ni/Al XPS ratio | Initial isobutylene yield (%) |
|---|---|---|
| 1 | ca 0.6 | 10–15 |
| 2 | 0.8 | 25–30 |
| 3 | ca 1.2 | 30–35 |

As shown in FIG. 5, the trend in catalyst deactivation correlates well with the dispersion of Cs. Although the sample treated with Procedure 2 had the highest initial activity, it deactivated more rapidly than the other two. The Procedure 2 sample exhibited some isomerization activity, which is an indication of residual acidity. This residual acidity may be responsible for the rapid deactivation and may be caused by a poorer distribution of Cs resulting from Procedure 2. Table 4 presents the data of FIG. 5 in tabular form.

TABLE 4

| Procedure | Cs/Al XPS ratio | Deactivation rate (% yield/hr) |
| --- | --- | --- |
| 1 | ca 0.1 | 0.4–0.4 |
| 2 | ca 0.06 | 0.7–0.8 |
| 3 | ca 0.11 | 0.3–0.4 |

Referring to FIG. 6, the reduced but unsulfided catalyst A (6%Ni/5%Cs-Al$_2$O$_3$, S/Ni ratio 0) exposed to a 0.5 H$_2$/isobutane feed produced only methane (black squares, selectivity to methane) and coked rapidly (open squares, carbon content on the catalyst after 10 hr under steady state reaction conditions). As increasing amounts of DMSO were added to the prereduced Ni catalyst, both the hydrogenolysis and coking rates drastically decreased. The carbon content measured after 10 hr onstream at 600° C. at a H$_2$/isobutane ratio of 0.5 dropped from almost 9 g C/g cat for the unsulfided Ni catalyst to almost 0 for catalyst exposed to a S/Ni ratio greater than 0.25. Likewise, the carbon molar selectivity towards methane decreased from 100% to less than 4%.

FIG. 7 shows isobutane dehydrogenation and deactivation relative rates as a function of H$_2$-isobutane molar ratio. The black squares show relative maximum rates of isobutane dehydrogenation, the white squares the relative deactivation rate, measured after the activation period, and the open circles the performance ratio, which is dehydrogenation/deactivation. As illustrated in FIG. 3, the optimal operating conditions in the case of sulfided nickel catalysts would be at a H$_2$/isobutane ratio of about 0.5.

The invention claimed is:

1. Process for dehydrogenating organic compounds which comprises: contacting a dehydrogenatable organic compound under dehydrogenation conditions with a catalyst prepared by oxidizing a composition comprising a catalytic metal selected from the group consisting of Group VIA, Group VIIIA first row and Group VIIIA second row metals and a nonacidic microporous support to obtain an oxidized composition, and sulfiding said oxidized composition.

2. Process according to claim 1 wherein said catalytic metal is a first-row Group VIIIA metal.

3. Process according to claim 2 wherein said catalytic metal is nickel.

4. Process according to claim 2 wherein said catalytic metal is a second-row Group VIIIA metal.

5. Process according to claim 4 wherein said catalytic metal is palladium.

6. Process according to claim 4 wherein said catalytic metal is rhodium.

7. Process according to claim 1 wherein said support is alumina.

8. Process according to claim 1 wherein said support is a zeolite.

9. Process according to claim 8 wherein said support is barium L zeolite.

10. Process according to claim 1 wherein said composition comprises a base.

11. Process according to claim 10 wherein said composition comprises alkali metal.

12. Process according to claim 11 wherein said alkali metal is cesium.

13. Process according to claim 1 wherein said sulfiding is in an atmosphere of hydrogen.

14. Process according to claim 1 wherein said oxidizing is at a temperature from about 250° to about 375° C.

15. Process for dehydrogenating organic compounds which comprises: contacting a dehydrogenatable organic compound under dehydrogenation conditions with a catalyst comprising sulfided nickel and nonacidic alumina, and having a ratio of the nickel 2P$_{3/2}$ peak area to the Al(2s) peak area, as determined by X-ray photoelectron spectroscopy of at least about 0.7, said ratio being determined by a spectrometer having an instrument transmission function inversely proportional to the kinetic energy of photoelectrons.

16. Process according to claim 15 wherein said ratio is at least about 0.8.

17. Process according to claim 16 wherein said ratio is at least about 1.

18. Process according to claim 15 wherein said catalyst comprises a base.

19. Process for dehydrogenating organic compounds which comprises: contacting a dehydrogenatable organic compound under dehydrogenation conditions with a catalyst comprising sulfided nickel and nonacidic alumina, and having a ratio of the sulfide S$^{2-}$(2p) peak area to the Al(2s) peak area, as determined by X-ray photoelectron spectroscopy of at least about 0.05, said ratio being determined by a spectrometer having an instrument transmission function inversely proportional to the kinetic energy of photoelectrons.

20. Process according to claim 19 wherein said composition comprises a base.

21. Process for dehydrogenating organic compounds which comprises: contacting a dehydrogenatable organic compound under dehydrogenation conditions with a catalyst comprising sulfided catalytic metal, a cesium compound and alumina, and having a ratio of the cesium 4P$_{3/2}$ peak area to the Al(2s) peak area, as determined by X-ray photoelectron spectroscopy of at least about 0.06, said ratio being determined by a spectrometer having an instrument transmission function inversely proportional to the kinetic energy of photoelectrons.

22. Process according to claim 21 wherein said ratio is at least about 0.08.

23. Process according to claim 22 wherein said ratio is at least about 0.1.

24. Process for dehydrogenating organic compounds which comprises: contacting a dehydrogenatable organic compound under dehydrogenation conditions with a catalyst comprising sulfided nickel and nonacidic alumina and having:

(1) a ratio of the nickel 2P$_{3/2}$ peak area to the Al(2s) peak area, as determined by X-ray photoelectron spectroscopy, of at least about 0.7, and/or (2) a ratio of the sulfide S$^{2-}$(2p) peak area to the Al(2s) peak area, as determined by X-ray photoelectron spectroscopy, of at least about 0.05;

said ratio being determined by a spectrometer having an instrument transmission function inversely proportional to the kinetic energy of photoelectrons.

25. Process according to claim 24 wherein said catalyst comprises cesium and has a ratio of the cesium 4P$_{3/2}$ peak area to the Al(2s) peak area, as determined by X-ray photoelectron spectroscopy, of at least about 0.07, said ratio being determined by a spectrometer having an instrument transmission function inversely proportional to the kinetic energy of photoelectrons XPS, of at least about 0.07.

* * * * *